US012571010B2

(12) United States Patent
Ko et al.

(10) Patent No.: US 12,571,010 B2
(45) Date of Patent: Mar. 10, 2026

(54) RECOMBINANT MICROORGANISM FOR PRODUCING POLY(3-HYDROXYBUTYRATE-CO-3-HYDROXYVALERATE)

(71) Applicant: KOREA INSTITUTE OF SCIENCE AND TECHNOLOGY, Seoul (KR)

(72) Inventors: Ja Kyong Ko, Seoul (KR); Youngyun Jo, Seoul (KR); Gyeongtaek Gong, Seoul (KR); Jung Ho Ahn, Seoul (KR); Sun Mi Lee, Seoul (KR); Youngsoon Um, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 636 days.

(21) Appl. No.: 18/059,330

(22) Filed: Nov. 28, 2022

(65) Prior Publication Data

US 2023/0313241 A1     Oct. 5, 2023

(30) Foreign Application Priority Data

Mar. 30, 2022   (KR) ........................ 10-2022-0039407

(51) Int. Cl.
| | |
|---|---|
| *C12P 7/625* | (2022.01) |
| *C12N 9/10* | (2006.01) |
| *C12N 15/74* | (2006.01) |

(52) U.S. Cl.
CPC ............ *C12P 7/625* (2013.01); *C12N 9/1022* (2013.01); *C12N 9/1029* (2013.01); *C12N 15/74* (2013.01); *C12Y 202/01006* (2013.01); *C12Y 203/01009* (2013.01); *C12Y 203/01182* (2013.01)

(58) Field of Classification Search
None
See application file for complete search history.

(56) References Cited

U.S. PATENT DOCUMENTS

2014/0248673 A1* 9/2014 Botes .................... C12P 13/002
                                     435/254.11

FOREIGN PATENT DOCUMENTS

| | | |
|---|---|---|
| KR | 10-0164288 B1 | 1/1999 |
| KR | 10-2021-0049865 A | 5/2021 |
| KR | 10-2361618 B1 | 2/2022 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Aramvash et al. International Journal of Biological Macromolecules. vol. 87, Jun. 2016, pp. 397-404 (Year: 2016).*
Ying-Zi Zhang et al., "Engineering of Ralstonia eutropha for the production of poly(3-hydroxybutyrate-co-3-hydroxyvalerate) from glucose," Journal of Biotechnology, 2015, vol. 195, pp. 82-88.
Quan Chen et al., "Production in Escherichia coli of Poly(3-Hydroxybutyrate-co-3-Hydroxyvalerate) with Differing Monomer Compositions from Unrelated Carbon Sources," Applied and Environmental Microbiology, 2011, vol. 77, No. 14, pp. 4886-4893.
Qian Wang et al., "Biosynthesis of poly(3-hydroxybutyrate-co-3-hydroxyvalerate) from glucose with elevated 3-hydroxyvalerate fraction via combined citramalate and threonine pathway in *Escherichia coli*," Applied Microbiology and Biotechnology, 2014, vol. 98, pp. 3923-3931.
The Request for the submission of an Opinion for Korean Patent Application No. 10-2022-0039407, dated Dec. 16, 2024.
Jung Eun Yang et al., "Metabolic engineering of *Escherichia coli* for biosynthesis of poly(3-hydroxybutyrate-co-3-hydroxyvalerate) from glucose," Appl Microbiol Biotechnol, 2013, pp. 95-104, vol. 98.
Carina Windhorst et al., "Efficient biochemical production of acetoin from carbon dioxide using Cupriavidus necator H16," Biotechnology for Biofuels, 2019, vol. 12, No. 163.

* cited by examiner

*Primary Examiner* — Christian L Fronda

(57) ABSTRACT

The present disclosure provides a recombinant microorganism for producing PHBV, a method for preparing the same, and a method for producing PHBV using the microorganism. The present disclosure may provide a recombinant microorganism capable of producing PHBV, which is a biodegradable plastic material with superior physical properties, directly from an inexpensive single carbon source with high efficiency without supplementation of organic acid. The present disclosure can enhance the utilization of PHA, which is expensive and has limited physical properties, and can also provide a technology more effective for industrialization using an inexpensive single carbon source. The PHBV produced according to an exemplary embodiment of the present disclosure can be used not only for general-purpose inexpensive products such as ecofriendly packing materials but also as a high-value-added medical biopolymer.

6 Claims, 6 Drawing Sheets

Specification includes a Sequence Listing.

RECOMBINANT MICROORGANISM FOR PRODUCING POLY(3-HYDROXYBUTYRATE-CO-3-HYDROXYVALERATE)

DESCRIPTION OF GOVERNMENT-SUPPORTED RESEARCH AND DEVELOPMENT

This research was conducted under the following government projects.

Ministry in charge: Ministry of Science and ICT, supervised and researched by: Korea Institute of Science and Technology, research project title: Support for research by Korea Institute of Science and Technology, research title: Development of next-generation high-efficiency energy materials technology, project No.: 2E31850, project ID: 1711173296.

Ministry in charge: Ministry of Science and ICT, supervised by: National Research Foundation of Korea, researched by: Korea Institute of Science and Technology, project title: Development of technology for climate change mitigation technologies, research title: Development of strain and biological process for producing medium- and long-chain fatty acids by converting unutilized biomass, project No.: 2020M1A2A2080847, project ID: 1711127810.

TECHNICAL FIELD

The present disclosure relates to a recombinant microorganism capable of producing a poly(3-hydroxybutyrate-co-3-hydroxyvalerate) copolymer (hereinafter, referred to as PHBV) and a method for producing a poly(3-hydroxybutyrate-co-3-hydroxyvalerate) copolymer using the same.

CROSS-REFERENCE TO RELATED APPLICATION

This application claims priority of Korean Patent Application No. 10-2022-0039407 filed on Mar. 30, 2022, the contents of which in their entirety are herein incorporated by reference.

REFERENCE TO AN ELECTRONIC SEQUENCE LISTING

The Sequence Listing created on Nov. 25, 2022 with a file size of 15,841 bytes, and filed herewith in xml file format as the file entitled "sequencelisting_457KCL0017US.xml," is hereby incorporated by reference in its entirety.

BACKGROUND ART

For a sustainable solution for the plastic waste issue, the need for replacing petroleum-based non-biodegradable plastics is increasing. Bioplastics are contrasted with the plastics prepared from fossil fuel-based monomers. Bioplastics are plastics produced from renewable raw materials and include biodegradable plastics that are degraded by bacteria.

Polyhydroxyalkanoates (PHAs), which are the main components of biodegradable bioplastics, are thermoplastic natural polyester polymers accumulated in the cells of microorganisms. Although they are marine biodegradable plastics that are compostable and generate no toxic wastes, PHAs have been used limitedly yet due to production cost and process instability issues. The existing PHA products have weaker physical properties as compared to petrochemically derived plastics. In order to overcome this disadvantage, bioplastics using various monomers are being studied. Polyhydroxybutyrate (PHB) polymerized from the $C_4$ monomer 3-hydroxybutyrate (3HB), which is known as the representative PHA polymer, has been researched a lot for commercial production because it has physical properties similar to those of polypropylene and can be synthesized relatively easily by microorganisms. However, it has hard and brittle properties due to high crystallinity and has limited processability. In order to compensate for this problem, blending with various materials and synthesis of PHA copolymers through copolymerization of various monomers have been researched.

The properties of PHA including biodegradability, biocompatibility, mechanical and chemical properties and molecular weight are often determined by the carbon source supplied to microorganisms, which affects the metabolic pathway of the microorganisms. That is to say, the final structure of PHA is determined by the PHA synthesis metabolic pathway which supplies monomers as the substrate of PHA synthase. The carbon sources are divided into carbon sources structurally related with PHA (organic acids) and other carbon sources (monosaccharides such as fructose, glucose, xylose, etc., carbon dioxide, etc.). Organic acids, which are carbon sources structurally similar to hydroxyalkanoic acids, are classified as structurally related carbon sources, and they are used to synthesize PHA copolymers with C5 or longer carbon chains. For example, for biosynthesis of 3-hydroxyvalarate, which is a precursor to PHBV, organic acids such as propionic acid, valeric acid, etc. are necessary as co-substrates. However, the organic acids are expensive substrates and may inhibit the growth of microorganisms by exhibiting toxicity when supplied at high concentrations.

DISCLOSURE

Technical Problem

The present disclosure is directed to providing a microorganism which directly produces PHBV using a single carbon source which is not structurally similar to PHA without supplementation of organic acid.

The present disclosure is also directed to providing a method for preparing a microorganism which directly produces PHBV using a single carbon source which is not structurally similar to PHA without supplementation of y organic acid.

The present disclosure is also directed to providing a method for producing PHBV directly by culturing the microorganism without supplementation of organic acid.

Technical Solution

In an exemplary embodiment, the present disclosure provides a recombinant microorganism transformed with a vector comprising an acetolactate synthase (alsS)-encoding gene, (R)-citramalate synthase (leuA)-encoding gene and an acetyl-CoA acetyltransferase (BktB)-encoding gene, wherein methylcitrate synthase-encoding genes prpC1 and prpC2 are deleted.

In an exemplary embodiment, the present disclosure provides a method for preparing the said recombinant microorganism, which comprises: a step of preparing a vector comprising an acetolactate synthase (alsS)-encoding gene, an (R)-citramalate synthase (leuA)-encoding gene and an acetyl-CoA acetyltransferase (BktB)-encoding gene; a step of deleting methylcitrate synthase-encoding genes prpC1 and prpC2 from a parental strain; and a step of transforming the parental strain with the methylcitrate synthase-encoding genes deleted by inserting the prepared vector.

In an exemplary embodiment, the present disclosure provides a method for producing a poly(3-hydroxybutyrate-co-3-hydroxyvalerate) (PHBV) copolymer, which comprises a step of culturing the said recombinant microorganism.

Advantageous Effects

In an exemplary embodiment, the present disclosure provides a recombinant microorganism for producing PHBV, a method for preparing the same, and a method for producing PHBV by using the microorganism. According to an exemplary embodiment, the recombinant microorganism can produce PHBV, which is a biodegradable plastic material with superior physical properties, directly from an inexpensive single carbon source with high efficiency without supplementation of organic acid. According to an exemplary embodiment, by introducing a PHBV synthesis pathway using acetolactate synthase to the microorganism through metabolic engineering, a method for producing biodegradable plastics containing 3HV at high content can be provided. The present disclosure can enhance the utilization of PHA, which is expensive and has limited physical properties, and can also provide a technology more effective for industrialization using an inexpensive single carbon source. The PHBV produced according to an exemplary embodiment of the present disclosure can be used not only for general-purpose inexpensive products such as ecofriendly packing materials but also as a high-value-added medical biopolymer.

BEST MODE

The exemplary embodiments of the present disclosure disclosed in the present specification are presented only for illustrative purposes. The exemplary embodiments of the present disclosure may be embodied in various forms and should not be interpreted as limiting the present disclosure. The present disclosure can be changed variously and may have various forms. The exemplary embodiments are not intended to limit the present disclosure but should be understood as including all changes, equivalents and substitutes encompassed within the technical idea and scope of the present disclosure. Singular expressions include plural expressions unless the context clearly dictates otherwise. In the present application, the terms "comprise (include)", "have", etc. specify the presence of stated features, materials, numbers, steps, operations, components or combinations thereof, but do not preclude the presence or addition of one or more other features, materials, numbers, steps, operations, components or combinations thereof.

In an exemplary embodiment, the present disclosure may provide a recombinant microorganism transformed with a vector comprising an acetolactate synthase (alsS)-encoding gene, an (R)-citramalate synthase (leuA)-encoding gene and an acetyl-CoA acetyltransferase (BktB)-encoding gene, wherein methylcitrate synthase gene-encoding prpC1 and prpC2 are deleted.

In an exemplary embodiment, the present disclosure may provide a method for preparing the recombinant microorganism described above, which comprises: a step of preparing a vector comprising an acetolactate synthase (alsS)-encoding gene, an (R)-citramalate synthase (leuA)-encoding gene and an acetyl-CoA acetyltransferase (BktB)-encoding gene; a step of deleting methylcitrate synthase-encoding genes prpC1 and prpC2 from a parental strain; and a step of transforming the parental strain with the methylcitrate synthase-encoding genes deleted by inserting the vector described above. The sequence of the introduction or deletion of the genes is not limited to that described in the present specification.

Figure 1:
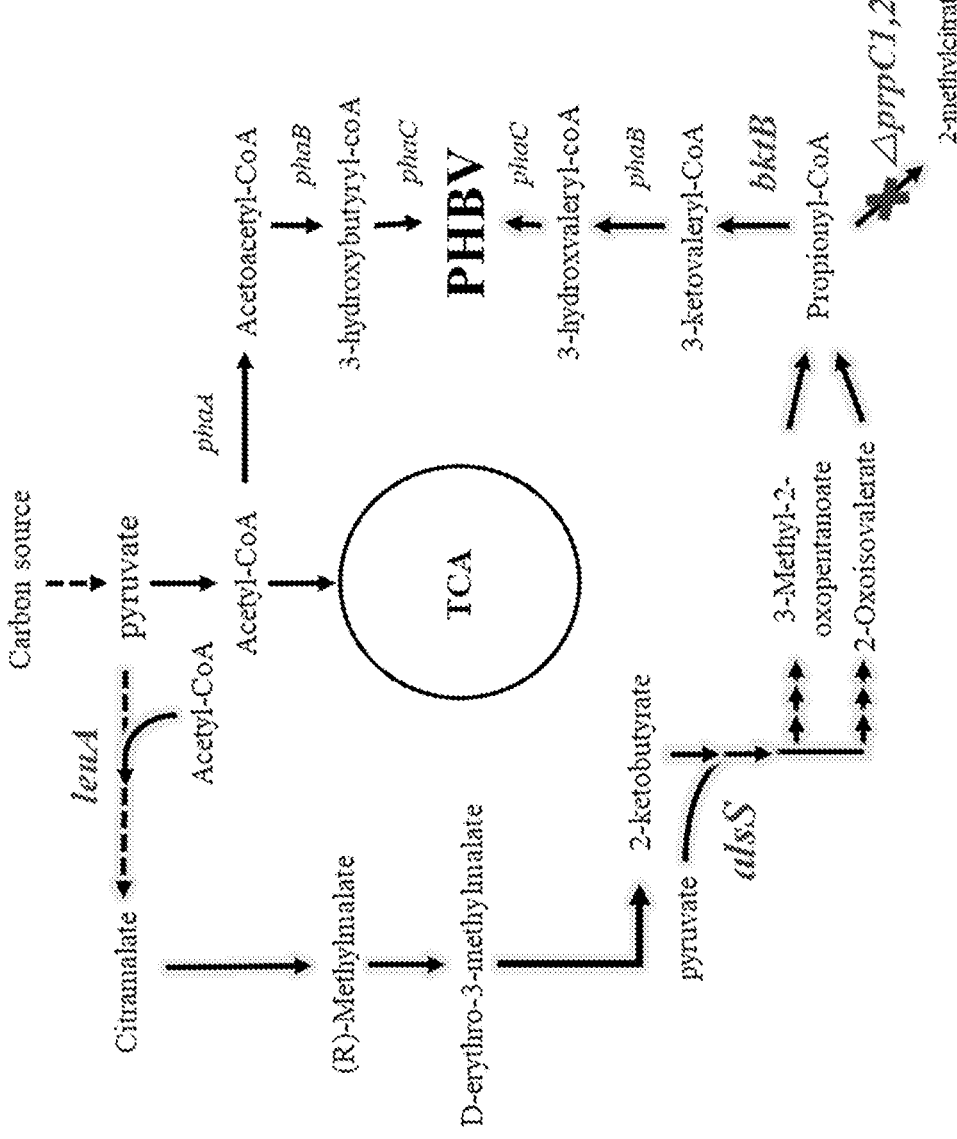
FIG. 1 shows the PHBV synthesis metabolic pathway of *Cupriavidus necator* wherein an acetolactate synthase (alsS)-encoding gene, an (R)-citramalate synthase (leuA)-encoding gene and an acetyl-CoA acetyltransferase (BktB)-encoding gene are introduced and prpC1- and prpC2-encoding genes are deleted.

FIG. 1 shows the PHBV synthesis metabolic pathway of *Cupriavidus necator* wherein an acetolactate synthase (alsS)-encoding gene, an (R)-citramalate synthase (leuA)-encoding gene and an acetyl-CoA acetyltransferase (BktB)-encoding gene are introduced and prpC1- and prpC2-encoding genes are deleted.

In an exemplary embodiment, the recombinant microorganism may be a transformed host microorganism, and the host microorganism may be a microorganism capable of producing PHB. For example, the host microorganism may be wild-type *Cupriavidus necator*. The wild-type *Cupriavidus necator* microorganism may be commercially available or may be acquired freely from a credible depository agency. In this aspect, the recombinant microorganism according to an exemplary embodiment may be recombinant *Cupriavidus necator*. Although *Cupriavidus necator* cannot produce PHBV on its own without supplementation of organic acid, it can be transformed to be capable of producing PHBV according to an exemplary embodiment. Since it can produce PHBV by using an inexpensive monosaccharide, carbon dioxide, etc. as a single carbon source, biodegradable plastics can be produced economically and sustainably.

In an exemplary embodiment, the acetolactate synthase (alsS)-encoding gene may be derived from Bacillus subtilis. In an exemplary embodiment, the acetolactate synthase (alsS)-encoding gene may consist of a sequence represented by SEQ ID NO 1.

In an exemplary embodiment, the (R)-citramalate synthase (leuA)-encoding gene may be derived from *Haloferax mediterranei*. The (R)-citramalate synthase-encoding gene may consist of a sequence represented by SEQ ID NO 2.

In an exemplary embodiment, the acetyl-CoA acetyltransferase (BktB)-encoding gene may be derived from *Cupriavidus necator*. The acetyl-CoA acetyltransferase-encoding gene may consist of a sequence represented by SEQ ID NO 3.

In the present specification, the "vector" refers to a gene construct comprising essential regulatory elements operably linked to express a gene insert encoding a target protein in a cell of a subject. It is a means of introducing a nucleic acid sequence encoding the target protein into a host cell. The vector may be one or more selected from a group consisting of a plasmid, a viral vector such as an adenoviral vector, a retroviral vector, an adeno-associated viral vector, etc., a bacteriophage vector, a cosmid vector and a YAC (yeast artificial chromosome) vector. The plasmid vector may be, for example, one or more selected from a group consisting of pBAD, pBBRMCS2, pJQ200mp18Km, pBluescript II KS(+), pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc. The bacteriophage vector may be, for example, one or more selected from a group consisting of lambda gt4, lambda B, lambda-Charon, lambda Δz1, M13, etc. The viral vector may be, for example, SV40, etc., although not being limited thereto. In the present specification, a "recombinant vector" comprises a cloning vector and an expression vector comprising a foreign target gene. The cloning vector is a replicon, which comprises an origin of replication, such as a plasmid, a phage or a cosmid, to which another DNA fragment may be attached so as to bring about the replication of the attached fragment. The expression vector is one developed for use in synthesis of proteins.

In the present specification, the vector is not specially limited as long as it can express and produce the desired enzyme gene in various host cells such as prokaryotic or eukaryotic cells. The gene delivered as being inserted in the vector may be fused irreversibly into genome of the host cell, so that gene expression in the cell can be maintained stably for a long time. The vector may comprise transcription and expression control sequences that allow the target gene to be expressed in the selected host. The expression control sequence may comprise a promoter for conducting transcription, an operator sequence for regulating the transcription, a sequence encoding a suitable ribosome-binding site of a mRNA and/or a sequence regulating the termination of transcription and translation. For example, a control sequence suitable for prokaryotes may comprise a promoter, an operator sequence and/or a ribosome-binding site. A control sequence suitable for eukaryotes may comprise a promoter, a terminator and/or a polyadenylation signal. A start codon and a stop codon are generally considered as parts of a nucleic acid sequence encoding a target protein. They should exhibit action when a gene construct is administered and should be in frame with a coding sequence. The promoter of the vector may be constitutive or inducible. And, a reproducible expression vector may comprise an origin of replication. In addition, it may adequately comprise an enhancer, untranslated regions of the 5' and 3' ends of the target gene, a selective marker (e.g., an antibiotic-resistant marker), a replicable unit, etc. The vector may self-replicate or may be incorporated into the host's genome DNA.

Useful expression control sequences comprise, for example, an araBAD promoter, a phaC1 promoter, a pj5 promoter, a lac system, a trp system, a TAC or TRC system, T3 and T7 promoters, major operator and promoter regions of phage lambda, the control region of the fd coat protein, promoters for phosphoglycerate kinase (PGK) or other glycolases, promoters of phosphatase, e.g., Pho5, α-matching systems of yeast, other sequences with different configurations or derivations known to control the gene expression of a prokaryotic or eukaryotic cell or their viruses, and various combinations thereof.

In order to increase the expression level of a gene transformed into a cell, the corresponding gene must be operably linked to an expression control sequence that performs transcription and translation. In general, "operably linked" means that DNA sequences being linked are contiguous and, in case of a secretory leader, they are contiguous and present in a reading frame. For example, a DNA for a pre-sequence or a secretory leader may be operably linked to a DNA for a polypeptide when it is expressed as a pre-protein that participates in the secretion of a protein. A promoter or an enhancer may be operably linked to a coding sequence when it affects the transcription of the sequence. A ribosome-binding site may be operably linked to a coding sequence when it affects the transcription of the sequence. Or, the ribosome-binding site may be operably linked to a sequence when it is disposed to facilitate translation. Linkage between the sequences may be performed by ligation in a convenient restriction enzyme site. When such a site does not exist, a synthetic oligonucleotide adaptor or a linker may be used according to a common method.

In an exemplary embodiment, the transformation may be performed using a suitable standard technology known in the art. For example, the transformation may be performed by heat shock transformation, electroporation, electroinjection, microinjection, calcium phosphate co-precipitation, calcium chloride/rubidium chloride method, retroviral infection, DEAE-dextran method, cationic liposome method, polyethylene glycol-mediated uptake, gene gun method, etc., although not being limited thereto.

In an exemplary embodiment, the recombinant microorganism may be cultured in a medium containing a single carbon source. In an exemplary embodiment, the "single carbon source" refers to a raw material that provides a carbon source needed by the strain for producing PHBV, and may be, for example, a monosaccharide comprising glucose and fructose, carbon dioxide, glycerol, etc. The monosaccharide is a carbon source that can be utilized by most organisms. It can be used for industrial culturing since it can be obtained easily in large quantities and is inexpensive. Carbon dioxide is produced as a byproduct in petrochemical processes. Because it is a greenhouse gas that causes global warming, its utilization by microorganisms will reduce carbon dioxide emission and enhance utilization of energy.

In an exemplary embodiment, the recombinant microorganism may be for producing a poly(3-hydroxybutyrate-co-3-hydroxyvalerate) (PHBV) copolymer. In an exemplary embodiment, the produced poly(3-hydroxybutyrate-co-3-hydroxyvalerate) copolymer may contain 3-hydroxyvalerate (3HV) at high content.

In the present specification, "polyhydroxyalkanoates (PHAs)" refer to thermoplastic natural polyester polymers accumulated in the cells of microorganisms. They are compostable biodegradable materials generating no toxic waste and are the only marine biodegradable plastic. The best known PHA-based polymer is polyhydroxybutyrate (PHB) polymerized from the $C_4$ monomer 3-hydroxybutyrate (3HB). Other PHAs comprise 3-hydroxy fatty acids with carbon chains of various lengths such as 3-hydroxyvalerate (3HV) and 3-hydroxyhexanoate (3HHx).

In an exemplary embodiment, the present disclosure may provide a method for producing a poly(3-hydroxybutyrate-co-3-hydroxyvalerate) (PHBV) copolymer, which comprises a step of culturing the recombinant microorganism described above.

In the present disclosure, the "culturing" may be performed by any method known in the art without limitation. In an exemplary embodiment, the microorganism may be cultured by any method selected from a group consisting of shaking culture, stationary culture, batch culture, fed-batch culture and continuous culture. The shaking culture refers to a method of culturing an inoculated culture of the microorganism while shaking, and the stationary culture refers to a method of culturing an inoculated liquid culture of the microorganism without shaking. The batch culture refers to a method of culturing the microorganism while fixing the volume of the culture without additional supply from outside, and the fed-batch culture refers to a method of culturing the microorganism by adding a small amount of nutrients in the beginning and then supplying them by piecemeal during the culturing, which is contrasted to batch culture of culturing the microorganism by putting all nutrients initially in the culture tank. The continuous culture refers to a method of culturing the microorganism by continuously supplying a fresh nutrient medium while continuously removing the culture containing cells and products.

In an exemplary embodiment, the culturing step may comprise culturing the recombinant microorganism in a medium containing a single carbon source. For example, the single carbon source may comprise one or more selected from a group consisting of carbon dioxide, glycerol, glucose, xylose, fructose, etc.

In an exemplary embodiment, the culturing may be performed in a common medium containing one or more selected from a group consisting of a nitrogen source, an amino acid, a vitamin, etc. in addition to the carbon source by controlling temperature, pH, etc. while satisfying the culturing requirement for the microorganism. For example, the medium may be an LB (Luria-Bertani) medium or a minimal medium. In an exemplary embodiment, the nitrogen source may be an inorganic nitrogen source such as ammonia, ammonium sulfate, ammonium chloride, ammonium acetate, ammonium phosphate, ammonium carbonate and ammonium nitrate, or an organic nitrogen source such as an amino acid, e.g., glutamic acid, methionine and glutamine, peptone, NZ-amine, meat extract, yeast extract, malt extract, corn steep liquor, casein hydrolysate, fish or degradation product thereof, soybean cake or degradation product thereof, etc. These nitrogen sources may be used either alone or in combination. The medium may contain monopotassium phosphate, dipotassium phosphate, corresponding sodium-containing salts, etc. as a phosphorus source. In an exemplary embodiment, the phosphorus source comprises potassium dihydrogen phosphate, dipotassium hydrogen phosphate or corresponding sodium-containing salts. In addition, an inorganic compound such as sodium chloride, potassium chloride, iron chloride, magnesium sulfate, iron sulfate, manganese sulfate, calcium carbonate, etc. may be used. Finally, a substance such as an amino acid or a vitamin may be further used. In an exemplary embodiment, the culture medium may contain a suitable precursor. The above-described ingredients may be added during batch culture, fed-batch culture or continuous culture according to a suitable method without special limitation. The pH of the culture may be controlled using a basic compound such as sodium hydroxide, potassium hydroxide or ammonia or an acidic compound such as phosphoric acid or sulfuric acid of a suitable concentration.

In an exemplary embodiment, the culturing step may comprise, after inoculating a PHBV-producing microorganism to the medium, culturing the microorganism within predetermined temperature and time ranges. For example, the microorganism may be cultured at a temperature of 20-40° C., specifically 25-35° C., more specifically 30° C. For example, the microorganism may be cultured for 48-120 hours.

In an exemplary embodiment, the production method may further comprise a step of separating the produced poly(3-hydroxybutyrate-co-3-hydroxyvalerate) copolymer from the culture after the culturing step. The separation step may further comprise a purification step. In an exemplary embodiment, the separation step may be performed by a method widely known in the art. For example, the separation may be performed by centrifugation, ultrasonic homogenization, organic solvent extraction, enzymatic, mechanical or chemical extraction, etc., although not being limited thereto.

In an exemplary embodiment, the produced poly(3-hydroxybutyrate-co-3-hydroxyvalerate) copolymer may contain 3-hydroxyvalerate (3HV) at high content. For example, it may contain 30 mol % or more, 35 mol % or more, 40 mol % or more, 45 mol % or more, 50 mol % or more, 55 mol % or more, 60 mol % or more, 65 mol % or more, 70 mol % or more, 75 mol % or more or 80 mol % or more of 3HV based on 100 mol % of the PHBV.

The PHBV produced according to an exemplary embodiment may be used as various biodegradable plastic materials such as biomaterials, packing materials, etc. The "biodegradable plastics" refer to polymers that release natural byproducts such as carbon dioxide, nitrogen, water, biomass, minerals, etc. after use, as plastics that can be degraded by bacteria or other organisms such as microorganisms.

Since the present disclosure allows effective production of PHBV having a high 3HV content, which can overcome the hard and brittle physical properties of the polyhydroxybutyrate (PHB) caused by high crystallinity, it can be utilized usefully in the field of biodegradable materials.

Hereinafter, the present disclosure is described in more detail referring to examples and drawings. However, the following examples and drawings are provided only to help the understanding of the present disclosure and the scope of the present disclosure is not limited by them.

EXAMPLE

Figure 2A:
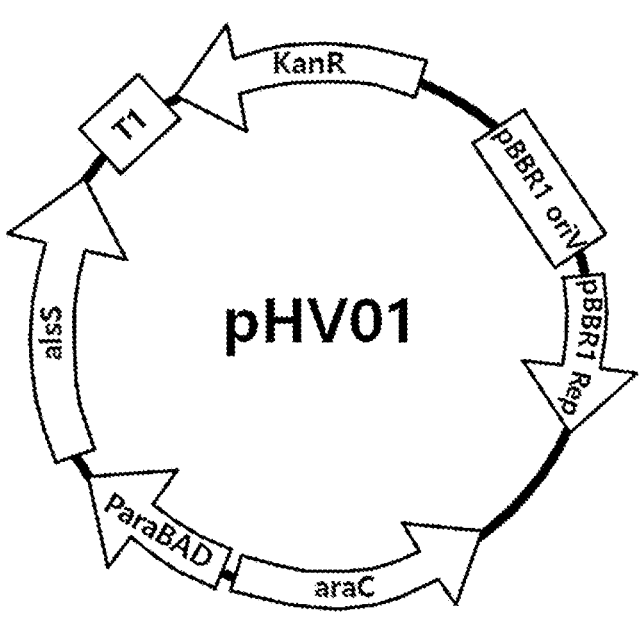
FIG. 2A shows the vector map of pBBR-MCS comprising alsS.
Figure 2B:
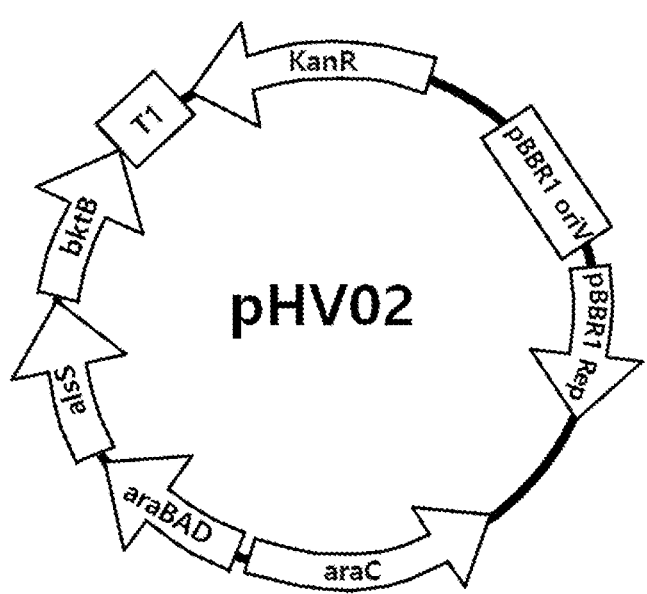
FIG. 2B shows the vector map of pBBR-MCS comprising alsS and BktB genes.
Figure 2C:
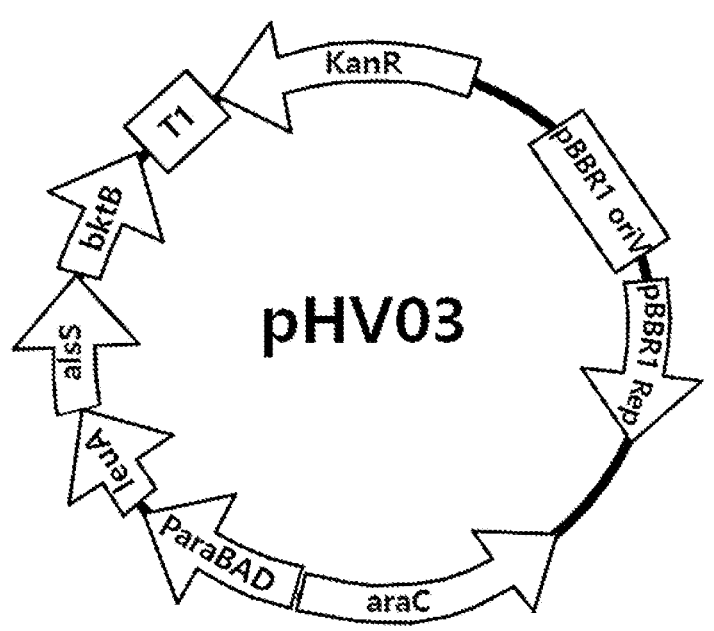
FIG. 2C shows the vector map of pBBR-MCS comprising alsS, BktB and leuA synthase genes.

Introduction of 3-hydroxyvalerate (3HV) Synthesis
Metabolic Pathway (i) For preparation of a vector (pHV01) comprising acetolactate synthase (alsS), an acetolactate synthase (alsS)-encoding gene (SEQ ID NO 1) was isolated and purified from the genome of *Bacillus subtilis* (ATCC 23857). The purified alsS gene was cloned into a pBBR-MCS plasmid wherein the transcription by an araBAD promoter (SEQ ID NO 4) was regulated by the addition of L-arabinose, as shown in FIG. 2A. The cloned plasmid (pHV01) was transformed into *E. coli* S-17 (ATCC 700926) using the heat shock method.

(ii) For preparation of a vector pHV02) comprising aceto-lactate synthase (alsS) and acetyl-CoA acetyltransferase (BktB), an acetolactate synthase-encoding gene was isolated and purified from the genome of *Cupriavidus necator* (ATCC 17699). A pBBR-MCS plasmid (pHV02) was pre-pared by comprising a ribosome-binding site (RBS, SEQ ID NO 5) between gene base sequences so that alsS and acetyl-CoA acetyltransferase (BktB) genes can be expressed together with one araBAD promoter. The prepared plasmid (pHV02) was transformed into *E. coli* S-17 (ATCC 700926) using the heat shock method.

(iii) For preparation of a vector (pHV03) comprising acetolactate synthase (alsS), acetyl-CoA acetyltransferase (BktB) and (R)-citramalate synthase (leuA), an (R)-citra-malate synthase (leuA)-encoding gene from the genome of *Haloferax mediterranei* was constructed into a synthetic gene to improve gene expression in consideration of the codon usage bias of *Cupriavidus necator*. A pBBR-MCS plasmid was prepared by comprising a ribosome-binding site (RBS, SEQ ID NO 5) between gene base sequences so that alsS-BktB and leuA genes can be expressed together with one araBAD promoter. The prepared pBBR-MCS plas-mid (pHV03) was transformed into *E. coli* S-17 (ATCC 700926) using the heat shock method.

Preparation of Strain with Methylcitrate Synthase Gene Deleted

A strain with only one of prpC1 and prpC2 deleted was prepared as follows. pJQ200mp18Km-prpC1 and pJQ200mp18Km-prpC2 were prepared by cloning 500-bp homologous base sequences upstream and downstream of prpC1 (SEQ ID NO 6) or prpC2 (SEQ ID NO 7), which are methylcitrate synthase-encoding genes to be deleted, into a pJQ200mp18Km plasmid by Gibson or overlap PCR. After transforming the pJQ200mp18Km-prpC1 or pJQ200mp18Km-prpC2 into *E. coli* S17-1 by the heat shock method, wild-type *Cupriavidus necator* (ATCC 17699) was transformed through conjugation. The *Cupriavidus necator* was cultured for 24 hours in an LB (Luria-Bertani) medium containing 200 μg/mL kanamycin. Then, the strain was spread onto a minimal medium agar plate containing 0.4% (w/v) sodium gluconate, 10 μg/mL gentamicin and 200 μg/mL kanamycin for 48 hours. After that, only the same single colonies were streaked on a minimal medium agar plate of the same condition. The single colonies streaked on the plate were incubated overnight in 5 mL of an LB medium containing 10 μg/mL gentamicin and 200 μg/mL kanamycin. Then, after incubation overnight in 5 mL of a low-sodium LB medium (2.5 g/L NaCl) containing 15% (w/v) sucrose, the single colonies were streaked on a low-sodium LB agar plate containing 15% (w/v) sucrose. After that, only the single colonies were streaked on a plate containing an antibiotic and a plate not containing an antibiotic. Finally, it was investigated whether the gene was deleted by conduct-ing PCR on the colonies on the plate containing no antibi-otic.

A strain with both the prpC1 and prpC2 genes deleted was prepared by the CRISPR-Cas9 method. The cas9 gene in a pCas9 (Addgene number 42876) plasmid was cloned into a pBBR-MCS plasmid. The corresponding sgRNA was tran-scribed from a constitutive promoter (SEQ ID NO 8). The sgRNA had a sequence represented by SEQ ID NO 9. After transforming the *Cupriavidus necator* (ATCC 17699) with the prpC2 gene deleted into a plasmid containing the pBBR-MCS-cas9-prpC1 sgRNA through conjugation, the single colonies were incubated for 72-120 hours in an LB medium containing 2 mg/mL arabinose and 200 μg/mL kanamycin. Then, they were spread on an LB plate containing arabinose and kanamycin of the same concentrations. Then, the plas-mid was removed after identifying the gene deletion was completed by colony PCR.

Preparation of Transformant

The pHV01, pHV02 and pHV03 plasmids were trans-formed into *E. coli* S-17 by the heat shock method. For the transformation, 10 μL of each plasmid (pHV01, pHV02 or pHV03), 70 μL of triply distilled water and 20 μL of a 5× KCM buffer (0.5N KCl, 0.15M $CaCl_2$, 0.25M $MgCl_2$) were added to an EP tube together with 100 μL of competent *E. coli* 10β cells and then cooled on ice for 10 minutes. Then, after conducting reaction on a heat block at 42° C. for 1 minute and 30 seconds, the cells were cooled on ice for 15 minutes. Subsequently, the cells were incubated at 37° C. for 1 hour after adding 1 mL of an LB medium. After centri-fuging the culture at 14000 rpm for 1 minute and removing 1 mL of the supernatant, the remaining supernatant and cell pellets were suspended. Then, 100 μL of the suspension was spread on an LB plate containing 50 μg/mL of kanamycin and reaction was conducted at 37° C. for 16 hours.

The plasmids introduced into the *E. coli* S-17 was trans-formed into *Cupriavidus necator* through conjugation. For the transformation, the *E. coli* S-17 strain into which the plasmid (pHV01, pHV02 or pHV03) was introduced and a *Cupriavidus necator* wild-type strain (WT), a mutant strain with the prpC1 gene deleted (ΔprpC1) or a mutant strain with both prpC1 and prpC2 genes deleted (ΔprpC1,2) were added to 10 mL of an LB medium. 200 μg/mL kanamycin was further added to the medium containing the *E. coli* strain. The medium containing the *E. coli* S-17 strain was incubated at 37° C. and the medium containing the *Cupria-vidus necator* wild-type strain (WT), the mutant strain with the prpC1 gene deleted (ΔprpC1) or a mutant strain with both prpC1 and prpC2 genes deleted (ΔprpC1,2) was incu-bated at 30° C., at 200 rpm for 20 hours. Subsequently, 1 mL of each culture was centrifuged at 14000 rpm for 1 minute. Then, after discarding the supernatant, the remaining cells were washed twice with 1 mL of 0.85% NaCl and then finally diluted to 1 mL. For conjugation, 20 μL of diluted *E. coli* S-17 cells and 30 μL of diluted *Cupriavidus necator* cells were mixed in a tube and incubated at 30° C. for 24 hours after spotting on an LB plate not containing an antibiotic. Then, half of the cell spot was scraped using a scraper and the cells were released in 300 μL of 0.85% NaCl. After that, they were spread on an LB plate containing 200 μg/mL kanamycin and 10 μg/mL gentamicin and incubated at 30° C. for 48 hours in order to identify the transformed *Cupriavidus necator*.

Culturing of Strain and Medium Composition

The transformed *Cupriavidus necator* strain was seed-cultured in an LB (Luria-Bertani) medium under an aerobic condition for 24 hours. Then, the cells seed-cultured for 24 hours were inoculated to a minimal medium and cultured under an aerobic condition ($OD_{600}$=0.2, 30° C., 200 rpm, induction with 0.2% L-arabinose 8 hours after culturing, cultured for a total of 96 hours). The *Cupriavidus necator* strain was cultured in a minimal medium containing 10 g/L fructose and 200 μg/mL kanamycin at 30° C. and 200 rpm. The final composition of the minimal medium was 6.74 g/L $Na_2HPO_4 \cdot 7H_2O$, 1.5 g/L $KH_2PO_4$, 0.5 g/L $(NH_4)_2SO_4$, 80 mg/L MgSO$_4$·7H$_2$O, 1 mg/L CaSO$_4$·2H$_2$O, 0.56 mg/L NiSO$_4$·7H$_2$O, 0.4 mg/L FeSO$_4$·7H$_2$O and 0.5 g/L NaHCO$_3$.

Test Example 1

Figure 3A:
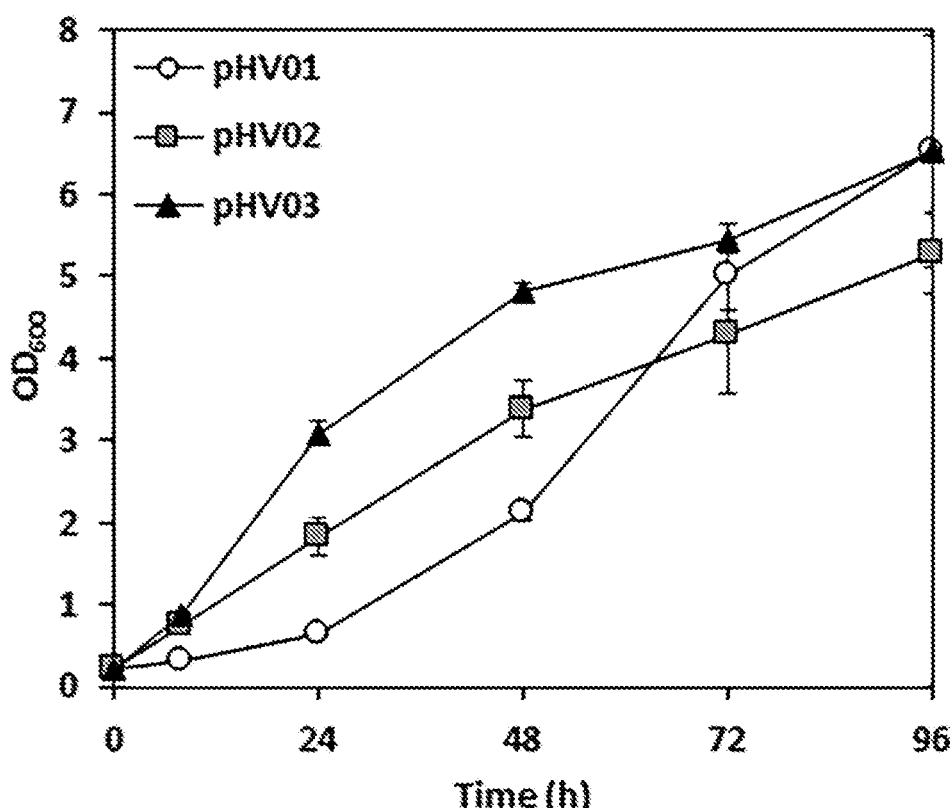
FIG. 3A shows the growth curves of recombinant strains obtained by transforming *Cupriavidus necator* with a prpC1 gene deleted with the vector of FIG. 2A (pHV01), the vector of FIG. 2B (pHV02) or the vector of FIG. 2C (pHV03) in the presence of fructose.
Figure 3B:
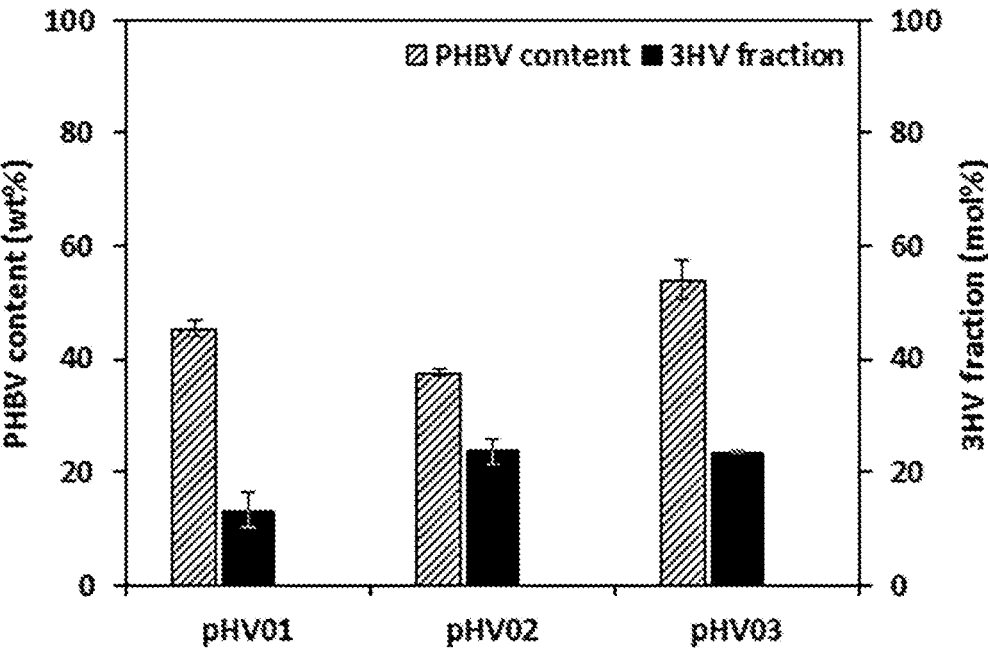
FIG. 3B shows the content of PHBV produced by recombinant strains obtained by transforming *Cupriavidus necator* with a prpC1 gene deleted with the vector of FIG. 2A (pHV01), the vector of FIG. 2B (pHV02) or the vector of FIG. 2C (pHV03).

In order to investigate difference depending on the genes introduced to the 3-hydroxyvalerate (3HV) synthesis metabolic pathway, recombinant strains were prepared by transforming the pHV01 vector, the pHV02 vector or the pHV03 vector described in Example into *Cupriavidus necator* with the prpC1 gene deleted, and they were cultured in a medium containing fructose as a single carbon source. Cell growth curves are shown in FIG. 3A, and the contents of produced PHBV are shown in FIG. 3B.

Specific analysis methods were as follows.

Extraction

The culture was centrifuged at 4200 rpm for 10 minutes. The cell pellets were stored in a deep freezer at −80° C. for 24 hours and then freeze-dried for 3 hours. 10 mg of the dried cell pellets were put in a screw-capped culture tube.

The methanolysis method was used for gas chromatography analysis. After adding 1 mL of chloroform or methanol containing 15% (v/v) sulfuric acid to the tube containing 10 mg of the dried cells and vortexing for 3 seconds, reaction was conducted in a water bath at 97° C. for 2 hours and 30 minutes. After the reaction, the mixture was vortexed for 3 seconds and then cooled on ice for 5 minutes. Then, after adding 1 mL of triply distilled water and chloroform containing 0.2% (v/v) methyl benzoate, the mixture was vortexed at 2400 rpm for 3 minutes. Subsequently, after centrifuging at 2000 rpm for 15 minutes, only the organic solution in the lower layer was subjected to gas chromatography-flame ionization detection (GC-FID) analysis.

GC Analysis

Analysis was conducted using a gas chromatography-flame ionization detection system (Agilent) and an HP-INNOWax column (30 m×0.320 mm×0.25 μm). Oven temperature was held at 80° C. for 2 minutes, raised to 245° C. at a rate of 10° C./min, and then held for 1 minute. Injector and detector temperatures were 250° C. and 275° C., respectively.

Calculation of PHBV and 3HV Contents

PHBV and 3HV contents were calculated as follows by using standard PHBV (3HV content: 8 mol %).

$$PHBV(\text{wt\%}) = 3HB(\text{wt\%}) + 3HV(\text{wt\%}) \qquad \text{[Equation 1]}$$

-continued $$3HB(\text{wt\%}) = \frac{\text{calculated value}}{\text{sample (mg)}} \times 100$$

$$3HV(\text{wt\%}) = \frac{\text{calculated value}}{\text{sample (mg)}} \times 100$$

$3HV$ fraction (mol%) =

$$\frac{3HV(\text{calculated value mol})}{3HV(\text{calculated value mol}) + 3HV(\text{calculated value mol})} \times 100$$

In the present specification, "OD$_{600}$" refers to the absorbance or optical density at a wavelength of 600 nm. It can be measured using an instrument such as a spectrophotometer. The density or concentration of microorganisms or cells in a solution or a sample may be identified from the measured OD$_{600}$.

As a result, it was confirmed that the strain with the pHV03 vector introduced can grow better than pHV02 under a culturing condition using fructose as a single carbon source since it comprises all the alsS, bktB and leuA genes, as shown in FIG. 3A. In addition, the strain with the pHV03 vector introduced showed the highest PHBV production in the cells since it comprises all the alsS, bktB and leuA genes, as shown in FIG. 3B.

Test Example 2

Figure 4A:
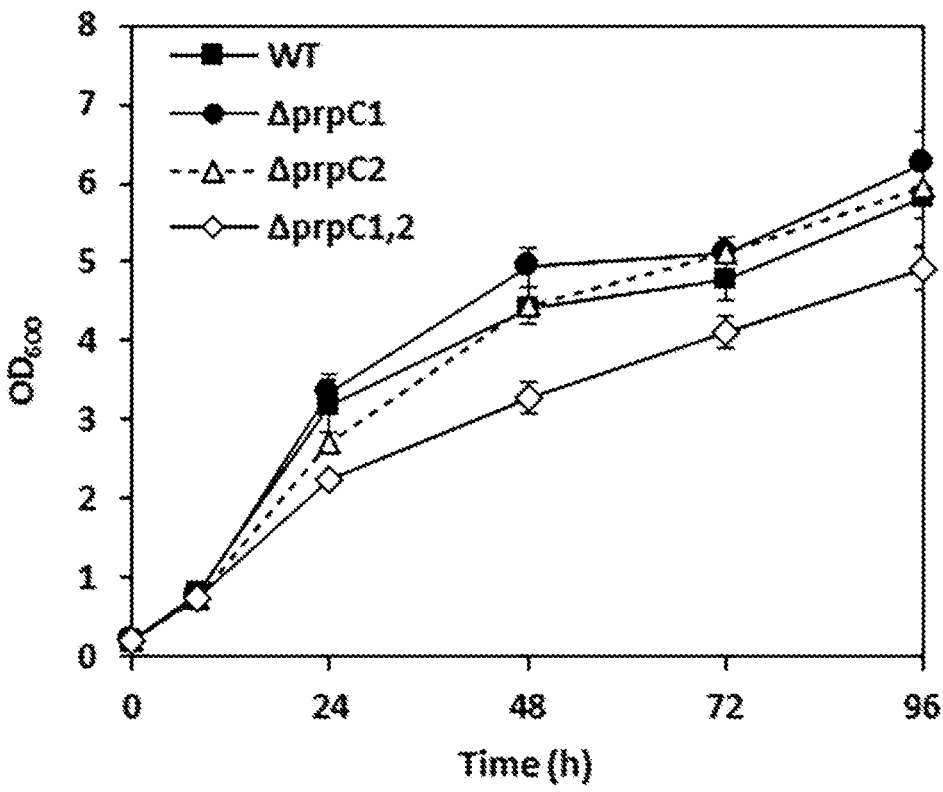
FIG. 4A shows the growth curves of recombinant strains obtained by transforming a wild-type *Cupriavidus necator* strain (WT), a transformed strain with a prpC1 gene deleted (ΔprpC1), a transformed strain with a prpC2 gene deleted (ΔprpC2), or a transformed strain with both prpC1 and prpC2 genes deleted (ΔprpC1,2), with the vector of FIG. 2C (pHV03) comprising alsS, BktB and leuA genes (pHV03) in the presence of fructose.
Figure 4B:
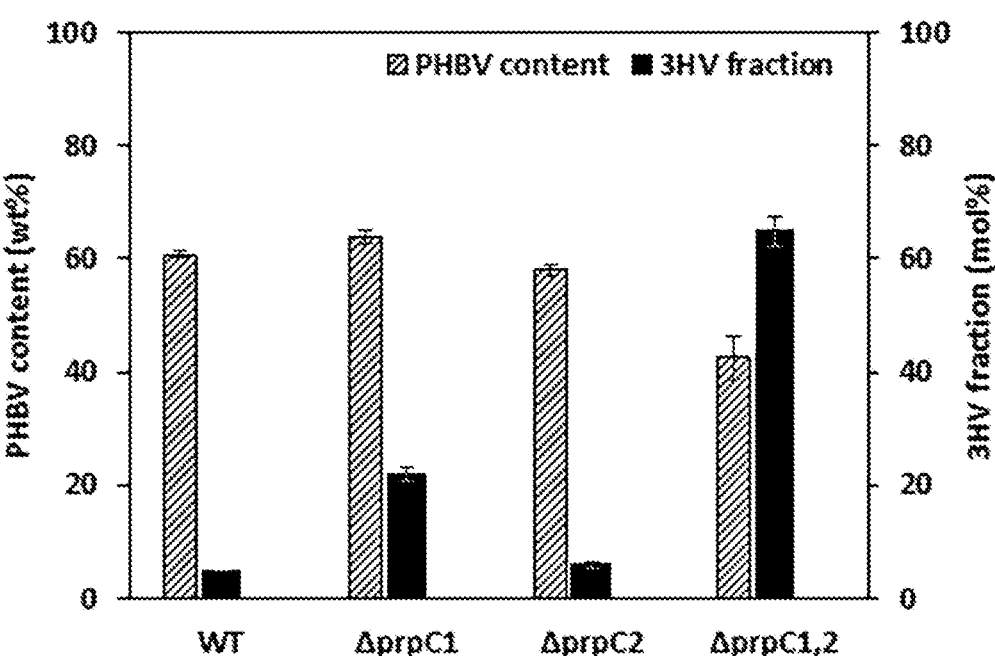
FIG. 4B shows the content of PHBV produced by the wild-type (WT), ΔprpC1, ΔprpC2 and ΔprpC1,2 recombinant strains of FIG. 4A.

In order to investigate difference depending on the methylcitrate synthase genes deleted in the transformed strain, recombinant strains were prepared by transforming the pHV03 vector into wild-type *Cupriavidus necator*, *Cupriavidus necator* with the prpC1 gene deleted, *Cupriavidus necator* with the prpC2 gene deleted, or *Cupriavidus necator* with both the prpC1 and prpC2 genes deleted according to the method described above and they were cultured in a medium containing fructose as a single carbon source. Their cell growth curves are shown in FIG. 4A, and the contents of PHBV produced during the culturing are shown in FIG. 4B. The analysis methods are the same as described in Test Example 1.

As a result, the *Cupriavidus necator* wild-type strain (WT), the mutant strain with the prpC1 gene deleted (ΔprpC1) and the mutant strain with the prpC2 gene deleted (ΔprpC2) showed faster growth as compared to the mutant strain with both the prpC1 and prpC2 genes deleted (ΔprpC1,2), as shown in FIG. 4A. However, as shown in FIG. 4B, the mutant strain with both the prpC1 and prpC2 genes deleted (ΔprpC1,2) showed a significantly higher content of 3HV in the PHBV at 60 mol % or more as compared to the strain with only one of prpC1 and prpC2 deleted.

Sequence Data

TABLE 1

| Sequence No. Name | Base sequence |
|---|---|
| 1 Acetolactate synthase, alsS | ttgacaaaagcaacaaaagaacaaaaatcccttgtgaaaaacagagggggcggagcttgttgttg attgcttagtggagcaaggtgtcacacatgtatttggcattccaggtgcaaaaattgatgcggt atttgacgctttacaagataaaggacctgaaattatcgttgcccggcacgaacaaaacgcagca ttcatggcccaagcagtcggccgtttaactggaaaaccgggagtcgtgttagtcacatcaggac cgggtgcctctaacttggcaacaggcctgctgacagcgaacactgaaggagaccctgtcgttgc gcttgctggaaacgtgatccgtgcagatcgtttaaaacggacacatcaatctttggataatgcg gcgctattccagccgattacaaaatacagtgtagaagttcaagatgtaaaaaatataccggaag ctgttacaaatgcatttaggatagcgtcagcagggcaggctggggccgctttttgtgagctttcc gcaagatgttgtgaatgaagtcacaaatacgaaaaacgtgcgtgctgttgcagcgccaaaactc |

TABLE 1-continued

| Sequence No. Name | Base sequence |
| --- | --- |
| | ggtcctgcagcagatgatgcaatcagtgcggccatagcaaaaatccaaacagcaaaacttcctg<br>tcgtttttggtcggcatgaaaggcggaagaccggaagcaattaaagcggttcgcaagcttttgaa<br>aaaggttcagcttccatttgttgaaacatatcaagctgccggtacccttttctagagatttagag<br>gatcaatattttggccgtatcggtttgttccgcaaccagcctggcgatttactgctagagcagg<br>cagatgttgttctgacgatcggctatgacccgattgaatatgatccgaaattctggaatatcaa<br>tggagaccggacaattatccatttagacgagattatcgctgacattgatcatgcttaccagcct<br>gatcttgaattgatcggtgacattccgtccacgatcaatcatatcgaacacgatgctgtgaaag<br>tggaatttgcagagcgtgagcagaaaatcctttctgatttaaaacaatatatgcatgaaggtga<br>gcaggtgcctgcagattggaaatcagacagagcgcaccctcttgaaatcgttaaagagttgcgt<br>aatgcagtcgatgatcatgttacagtaacttgcgatatcggttcgcacgccatttggatgtcac<br>gttatttccgcagctacgagccgttaacattaatgatcagtaacggtatgcaaacactcggcgt<br>tgcgcttccttgggcaatcggcgcttcattggtgaaaccgggagaaaaagtggtttctgtctct<br>ggtgacggcggtttcttattctcagcaatggaattagagacagcagttcgactaaaagcaccaa<br>ttgtacacattgtatggaacgacagcacatatgacatggttgcattccagcaattgaaaaaata<br>taaccgtacatctgcggtcgatttcggaaatatcgatatcgtgaaatatgcggaaaatgaacgc<br>tgaaggtcctgtcatcatcgatgtcccggttgactacagtgataacattaatttagcaagtgac<br>aagcttccgaaagaattcggggaactcatgaaaacgaaagctctctag |
| 2 (R)-<br>Citramalate<br>synthase,<br>leuA | gtgaacgtacgattcgggaagaccccccgagctacgcacttttgatttgggacggcgtgtccgtta<br>tgacactagccgacggggagcatcagcgcggcgtttggccgtcgccggtcgtgaatcagggcat<br>cgtccgcgtgctcgcccgcgtccgcgctcgcttgcatcgtagcgggaagcgcttgcaccgttccc<br>ggcgtgcgcgaaatcatcaagcgcgtcatgtcgctggcccgcgacgtgacggtgacgagtttcg<br>tccgcggcgtccaaagcgtcatcgtccgcgcactcgtttgcgtcgtcgtcggcatcatgcgcgt<br>cgttccgtcgagtgaccgccacgtcgagtcgaatcgcggcatcatccgcaagggtgtcgttcag<br>atgatcgccgtactcgtcgtgtacgccaaggaccacggcctgtgggtcgcggtcatcggcggcg<br>tcggttgagtcgcgccgccggagtttcgcgtcgcactcgcacgaaccagccacgtcgttggggg<br>gaccgattttgtttcgtcgtcatggtcgtccgcatcagccgcgcgcacactacgatgtcgtttt<br>gtcggctcgtggaactcgggccgacatcgacccacacgcacgtcgtcctcggactcgtcatggc<br>gaacgtacgcgccagtgtggccgcgggagcggacctcgtccacgccatggtcaacggcatcggc<br>gagcgcgtcggcaacgtcgtactcgacgcggtcgctatcgcgccggcgcactgttgcgccgccg<br>tgtcggtgaaacagcacgaattctacgcgcgtggctcagaaggtcgctcactcgacgggcgtttc<br>gcttccgccgaacaaggccgagcagcgcgcgtacgccttcacccacgaaagcggcatccacacc<br>gacgcgcacgctcaaagacgacgcgatgtacgaaccctacccgccggcgtcggtgggtcgtcagc<br>gtcgcgagctccagcgtaaacacgctggacgcgcgggtgtcaaggccgctctcgacgaacacgg<br>cgtcgacgcaaccggcgaggaagtcgcccgccgtcgtcgaacgagtgaaagaactcggcgaccgc<br>ggaaaacgcgtcaccgacgccgacctcctcgcgttcgcagaagacgtacaggggcacgaaccg<br>aacgacaggtcgaactcctcgacctcacggccgcctccggcgggggactccgactgcaagcgtc<br>agactccgcgtagagggcgaagaatgcgagccctccggaattggctccggcccggttgacgccg<br>cggtgaaagcagttcggcaggccctcggttccgacgccgacgcacaactcgacgactaccacgt<br>cgacgccatcaccggtgggaccgacgcggtcgtcaccgtcgaagtaaccatgtctcacgcgac<br>cgaagcgagccagtcgccgccgcgtacgcggacatcacccgtgcgagcgtgcaggcgatggagc<br>atgcgctcgaccgacttctcgcgccgggccataccgctgcgtcaccagcatcggccgacgactg<br>a |
| 3 Acetyl-CoA<br>acetyl-<br>transferase,<br>BktB | atgacgcgtgaagtggtagtggtaagcggtgtccgtaccgcgatcgggacctttggcggcagcc<br>tgaaggatgtggcaccggcggagctgggcgcactggtggtgcgcgaggcgctggcgcgcgcgca<br>ggtgtcgggcgacgatgtcggccacgtggtattcggcaacgtgatccagaccgagccgcgcgac<br>atgtatctgggccgcgtcgcggccgtcaacggcgggtgacgatcaacgcccccgcgctgaccg<br>tgaaccgcctgtgcggctcgggcctgcaggccattgtcagcgccgcgcagaccatcctgctggg<br>cgataccgacgtcgccatcggcggcggcgcggaaagcatgagccgcgcaccgtacctggcgccg<br>gcagcgcgctggggcgcacgcatgggcgacgccggcctggtcgacatgatgctgggtgcgctgc<br>acgatcccttccatcgcatccacatgggcgtgaccgccgagaatgtcgccaaggaatacgacat<br>ctcgcgcgcgcagcaggacgaggccgcgctggaatcgcaccgccgcgcttcggcagcgatcaag<br>gccggctacttcaaggaccagatcgtcccggtggtgagcaagggccgcaagggcgacgtgacct<br>tcgacaccgacgagcacgtgcgccatgacgcgccaccatcgacgacatgaccaagctcaggccggt<br>cttcgtcaaggaaaacgcgacggtcacggccggcaatgcctcgggcctgaacgacgccgacgcc<br>gcggtggtgatgatggagcgcgccgaagccgagccgcgcggcctgaagccgctggcccgcctgg<br>tgtcgtacggccatgccggcgtggacccgaaggccatgggcatcggcccggtgccggcgacgaa<br>gatcgcgctggagcgcgccggcctgcaggtgtcggacctggacgtgatcgaagccaacgaagcc<br>tttgccgcacaggcgtgcgccgtgaccaaggcgctcggtctggaccccggccaaggttaacccga<br>acggctcgggcatctcgctgggccacccgatcggcgccaccggtgccctgatcacggtgaaggc<br>gctgcatgagctgaaccgcgtgcagggcgctacgcgctggtgacgatgtgcatcggcggcggg<br>cagggcattgccgccatcttcgagcgtatctga |
| 4 araBAD<br>promoter | aagaaaccaattgtccatattgcatcagacattgccgtcactgcgtcttttactggctcttctc<br>gctaaccaaaccggtaaccccgcttattaaaagcattctgtaacaaagcgggaccaaagccatg<br>acaaaaacgcgtaacaaaagtgtctataatcacggcagaaaagtccacattgattatttgcacg<br>gcgtcacactttgctatgccatagcattttttatccataagattagcggattctacctgacgctt<br>tttatcgcaactctctactgtttctccat |
| 5 Ribosome<br>binding site | acaaccaaaggaggacaacc |
| 6 Methyl<br>citrate<br>synthase<br>prpC1 | atgtccgaagcgcaaccgctcgtcactcccaagcccaagaaatccgtcgccctgtcgggcgtga<br>ccgccggcaataccgcgctgtgcaccgtcggccgcactggcaacgacctgcactaccgcgcgcta<br>cgacatcctcgacatcgccgagacctgcgagttcgaggaaatcgcccacctgctggtgcacggc<br>aagctgccgaccaaatccgaactggccgcctacaaggcaaagctcaagagcctgcgcgcggcctgc |

TABLE 1-continued

| Sequence No. Name | Base sequence |
|---|---|
| | ccgccaatgtgaaggccgcgttggaatgggtgcccgccagcgcccacccgatggacgtgatgcg caccggcgtgtcggtgctgggcaccgtgctgccggagaaggaagaccacaacaccccggtacag ccacaacggccgccgtatcgaagtcgaaaccgacgatgactccatcggcggccacttcctgcac ctgctgcacggcgagaagccgtcggccgctgtgggagcgcgccatgaacacctcgctcaacctgt acgccgagcacgagttcaacgcctcgaccttcaccgcccgcgtgatcgccggcacgggctcgga catgtattcgtcgatcagcggcgccatcggcgcactgcgcggccccaagcacggcggcgccaat gaagtcgcgttcgagatccagaagcgctacgacaaccccgacgaggcccaggccgacatcacgc gccgcgtcgagaacaaggaagtcgtgatcggcttcggccacccggtgtacaccaccggcgaccc gcgcaaccaggtgatcaaggaagtggcgaagaagctgtcgaaggatgccggctcgatgaagatg tttgacatcgccgagcgcctggaaacggtgatgtgggacatcaagaagatgttcccgaacctgg actggttcagcgcggtgagctaccacatgatgggcgtgccgacggcgatgttcacgccgctgtt cgtgatcgcgcgtacttcgggctgggccgcgcacattatcgagcagcgcatcgacaacaagatc atccgcccgagcgcccaactacaccggtccggagaacctgaagttcgtgccgctgaaggatcgca agtaa |
| 7 Methyl citrate synthase prpC2 | atgtccgcctcgaagttcgccgcacccgacgctgcacccgacgccacggccagcgagccggccg cgccccgggtcaagaaatccgtcgccctgtcgggcgtgaccgccggcaataccgcgctgtgcac cgtcggccgcaccggcaacgacctgcactaccgcggctacgacatcctcgacatcgccgagacc tgcgagttcgaggaaatcgcccacctgctggtacacggcaagctgccgaccaaatccgaactgg ccgcctacaaggccaagctcaagagcctgcgcggcctgcccgccaatgtgaaggccgcgttgga atgggtgcccgccagcgcccacccgatggacgtgatgcgcaccggcgtgtcggtgctgggcacc gtgctgccggagaaggaagaccacaacaccccgggcgcgacgacattgccgaccggctgatgg ccagcctcggctcgatgctgctgtactggtaccactacagccacaacggccgccgctatcgaagt cgaaaccgacgatgactccatcggcggccacttcctgcacctgctgcacggcgagaagccgtcg gcgctgtgggagcgcgccatgcacacctcgctcaacctgtacgccgagcacgagttcaacgcct cgaccttcaccgcccgcgtgatcgccggcacgggctcggacatgtattcgtcgatcagcggcgc catcggcgcgctgcgcggccccaagcacggcggcgccaatgaagtcgcgttcgagatccagaag cgctacgacaaccccgacgaggcccaggccgacatcacgcgccgcgtcgagaacaaggaagtcg tgatcggcttcggccacccggtgtacaccaccggcgacccgcgcaaccaggtgatcaaggaagt ggcgaagaagctgtctaaggatgccggctcgatgaagatgttcgacatcgccgagcgcctggaa acggtgatgtgggacatcaagaagatgttcccgaacctggactggttcagcgcggtgagctacc acatgatgggcgtgccgacggcgatgttcacgccgctgttcgtgatcgcgcgtacttcgggctg ggccgcgcacattatcgagcagcgcatcgacaacaagatcatccgcccgagcgccaactacacc ggtccggagaacctgaagttcgtgccgatcggcaagcgcaagtga |
| 8 Constitutive promoter | ctaggtttatacataggcgagtactctgttatggagtcagatcttagc |
| 9 sgRNA | tcggctcgatgctgctgtac |

The present disclosure may provide the following embodiments.

Embodiment 1

A recombinant microorganism transformed with a vector comprising an acetolactate synthase (alsS)-encoding gene, an (R)-citramalate synthase (leuA)-encoding gene and an acetyl-CoA acetyltransferase (bktB)-encoding gene, wherein methylcitrate synthase-encoding genes prpC1 and prpC2 are deleted.

Embodiment 2

The recombinant microorganism according to the embodiment 1, wherein the recombinant microorganism is recombinant *Cupriavidus necator.*

Embodiment 3

The recombinant microorganism according to the embodiment 1 or 2, wherein the acetolactate synthase (alsS)-encoding gene is derived from *Bacillus subtilis.*

Embodiment 4

The recombinant microorganism according to any of the embodiments 1-3, wherein the (R)-citramalate synthase (leuA)-encoding gene is derived from *Haloferax mediterranei.*

Embodiment 5

The recombinant microorganism according to any of the embodiments 1-4, wherein the acetyl-CoA acetyltransferase (bktB) encoding gene is derived from *Cupriavidus necator.*

Embodiment 6

The recombinant microorganism according to any of the embodiments 1-5, wherein the recombinant microorganism is cultured in a medium containing a single carbon source.

Embodiment 7

The recombinant microorganism according to any of the embodiments 1-6, wherein the recombinant microorganism is for producing a poly(3-hydroxybutyrate-co -3-hydroxyvalerate) (PHBV) copolymer.

Embodiment 8

A method for preparing the recombinant microorganism according to any of the embodiments 1-7, which comprises:
   a step of preparing a vector comprising an acetolactate synthase (alsS)-encoding gene, an (R)-citramalate synthase (leuA)-encoding gene and an acetyl-CoA acetyltransferase (bktB)-encoding gene;
   a step of deleting methylcitrate synthase-encoding genes prpC1 and prpC2 from a parental strain; and a step of transforming the parental strain with the methylcitrate synthase-encoding genes deleted by inserting the vector.

Embodiment 9

A method for producing a poly(3-hydroxybutyrate-co-3-hydroxyvalerate) (PHBV) copolymer, which comprises a step of culturing the recombinant microorganism according to any of the embodiments 1-7.

Embodiment 10

The production method according to the embodiment 9, wherein the culturing step comprises culturing the recombinant microorganism in a medium containing a single carbon source.

Embodiment 11

The production method according to the embodiment 9 or 10, wherein the single carbon source comprises one or more selected from a group consisting of carbon dioxide, glucose, xylose, fructose and glycerol.

Embodiment 12

The production method according any of the embodiments 8-11, wherein the produced poly(3-hydroxybutyrate-co-3-hydroxyvalerate) copolymer comprises 30 mol % or more of 3-hydroxyvalerate (3HV).

---

The invention claimed is:

1. A recombinant microorganism transformed with a vector comprising an acetolactate synthase (αlsS)-encoding gene, an (R)-citramalate synthase (leuA)-encoding gene and an acetyl-CoA acetyltransferase (bktB)-encoding gene, wherein methylcitrate synthase-encoding genes prpC1 and prpC2 are deleted, wherein the alsS-encoding gene consists of the nucleotide sequence of SEQ ID NO: 1, wherein the leuA-encoding gene consists of the nucleotide sequence of SEQ ID NO: 2, wherein the BktB-encoding gene consists of the nucleotide sequence of SEQ ID NO: 3, wherein the prpC1 consists of the nucleotide sequence of SEQ ID NO: 6, wherein the prpC2 consists of the nucleotide sequence of SEQ ID NO: 7, and wherein the recombinant microorganism is recombinant *Cupriavidus necator*, and wherein the recombinant *Cupriavidus necator* produces a 3-hydroxyvalerate (3HV) in a poly(3-hydroxybutyrate-co-3-hydroxyvalerate) (PHBV) copolymer at 60 mol % or more when cultured in a medium comprising fructose.

2. The recombinant microorganism according to claim 1, wherein the acetolactate synthase (alsS)-encoding gene is derived from *Bacillus subtilis*.

3. The recombinant microorganism according to claim 1, wherein the (R)-citramalate synthase (leuA)-encoding gene is derived from *Haloferax mediterranei*.

4. The recombinant microorganism according to claim 1, wherein the acetyl-CoA acetyltransferase (bktB)-encoding gene is derived from *Cupriavidus necator*.

5. The recombinant microorganism according to claim 1, wherein the recombinant microorganism is cultured in a medium comprising a single carbon source.

6. The recombinant microorganism according to claim 1, wherein the recombinant microorganism is for producing a poly(3-hydroxybutyrate-co-3-hydroxyvalerate) (PHBV) copolymer.

* * * * *

SEQUENCE LISTING

```
Sequence total quantity: 9
SEQ ID NO: 1            moltype = DNA  length = 1713
FEATURE                 Location/Qualifiers
source                  1..1713
                        mol_type = other DNA
                        organism = unidentified
SEQUENCE: 1
ttgacaaaag caacaaaaga acaaaaatcc cttgtgaaaa acagaggggc ggagcttgtt  60
gttgattgct tagtggagca aggtgtcaca catgtatttg gcattccagg tgcaaaaatt  120
gatgcggtat ttgacgcttt acaagataaa ggacctgaaa ttatcgttgc ccggcacgaa  180
caaaacgcag cattcatggc ccaagcagtc ggccgtttaa ctggaaaacc gggagtcgtg  240
ttagtcacat caggaccggg tgcctctaac ttggcaacag gcctgctgac agcgaacact  300
gaaggagacc ctgtcgttgc gcttgctgga aacgtgatcc gtgcagatcg tttaaaacgg  360
acacatcaat cttgggataa tgcggcgcta ttccagccga ttacaaaata cagtgtagaa  420
gttcaagatg taaaaaatat accggaagct gttacaaatg catttaggat agcgtcagca  480
gggcaggctg gggccgcttt tgtgagcttt ccgcaagatg ttgtgaatga agtcacaaat  540
acgaaaaacg tgcgtgctgt tgcagcgcca aaactcggtc ctgcagcaga tgatgcaatc  600
agtgcggcca tagcaaaaat ccaaacagca aaacttcctg tcgttttggt cggcatgaaa  660
ggcggaagac cggaagcaat taaagcggtt cgcaagcttt tgaaaaaggt tcagcttcca  720
tttgttgaaa catatcaagc tgccggtacc ctttctagag atttagagga tcaatatttt  780
ggccgtatcg gtttgttccg caaccagcct ggcgatttac tgctagagca ggcagatgtt  840
gttctgacga tcggctatga cccgattgaa tatgatccga aattctggaa tatcaatgga  900
gaccggacaa ttatccattt agacgagatt atcgctgaca ttgatcatgc ttaccagcct  960
gatcttgaat tgatcggtga cattccgtcc acgatcaatc atatcgaaca cgatgctgtg  1020
aaagtggaat ttgcagagcg tgagcagaaa atcctttctg atttaaaaca atatatgcat  1080
gaaggtgagc aggtgcctgc agattggaaa tcagacagag cgcaccctct tgaaatcgtt  1140
aaagagttgc gtaatgcagt cgatgatcat gttacagtaa cttgcgatat cggttcgcac  1200
gccatttgga tgtcacgtta tttccgcagc tacgagccgt aacattaat gatcagtaac  1260
ggtatgcaaa cactcggcgt tgcgcttcct tgggcaatcg gcgcttcatt ggtgaaaccg  1320
ggagaaaaag tggtttctgt ctctggtgac ggcggtttct tattctcagc aatggaatta  1380
gagacagcag ttcgactaaa agcaccaatt gtacacattg tatggaacga cagcacatat  1440
gacatggttg cattccagca attgaaaaaa tataaccgta catctgcggt cgatttcgga  1500
aatatcgata tcgtgaaata tgcggaaagc ttcggagcaa ctggcttgcg cgtagaatca  1560
ccagaccagc tggcagatgt tctgcgtcaa ggcatgaacg ctgaaggtcc tgtcatcatc  1620
gatgtcccgg ttgactacag tgataacatt aatttagcaa gtgacaagct tccgaaagaa  1680
ttcggggaac tcatgaaaac gaaagctctc tag                              1713

SEQ ID NO: 2            moltype = DNA  length = 1539
FEATURE                 Location/Qualifiers
source                  1..1539
                        mol_type = other DNA
                        organism = unidentified
SEQUENCE: 2
gtgaacgtac gattcgggaa gacccccgag ctacgcactt ttgatttggg acggctgtcc  60
gttatgacac tagccgacgg ggagcatcag cgcggcgttt ggccgtcgcc ggtcgtgaat  120
cagggcatcg tccgcgtgct cgcccgcgtc cgcgtcgctt gcatcgtagc gggaagcgct  180
tgcaccgttc ccgcgcgtgcg cgaaatcatc aagcgcgtca tgtcgctggc ccgcgacgtg  240
acggtgacga gtttcgtccg cggcgtccaa agcgtcatcg tccgcgcact cgtttgcgtc  300
gtcgtcggca tcatgcgcgt cgttccgtcg agtgaccgcc acgtcgagtc gaatcgcggc  360
atcatccgca agggtgtcgt tcagatgatc gccgtactcg tcgtgtacgc caaggaccac  420
ggcctgtggg tcgcggtcat cggcgcgcgtc ggttgagtcg cgccgccgga gtttcgcgtt  480
gcactcgcac gaaccagcca cgtcgttggg gcggaccgat tttgtttcgt cgtcatggtc  540
gtccgcatca gccgcgcgca cacgtacgat gtcgtttgtc ggctcgtgga actcgggccg  600
acatcgaccc acacgcacgt cgtcctcgga ctcgtcatgg cgaacgtacg cgccagtgtg  660
gccgcgggag cggacctcgt ccacgccatg gtcaacggca tcggcgagcg cgtcggcaac  720
gtcgtactcg acgcggtcgc tatcgcgccg gcgcactgtt gcgccgccgt gtcggtgaaa  780
```

-continued

```
cagcacgaat tctacgcgct ggctcagaag gtcgctcact cgacgggcgt ttcgcttccg   840
ccgaacaagg ccgagcagcg cgcgtacgcc ttcacccacg aaagcggcat ccacaccgac   900
ggcacgctca aagacgacgc gatgtacgaa ccctacccgc cggcgtcggt gggtcgtcag   960
cgtcgcgagc tccagcgtaa acacgctgga cgcgcgggtg tcaaggccgc tctcgacgaa  1020
cacggcgtcg acgcaaccgg cgaggaagtc gccgccgtcg tcgaacgagt gaaagaactc  1080
ggcgaccgcg gaaaacgcgt caccgacgcc gacctcctcg cgttcgcaga agacgtacag  1140
gggcacgaac gcgaacgaca ggtcgaactc ctcgacctca cggccgcctc cggcggcggg  1200
actccgactg caagcgtcag actccgcgta gagggcgaag aatgcgagcc ctccggaatt  1260
ggctccggcc cggttgacgc cgcggtgaaa gcagttcggc aggccctcgg ttccgacgcc  1320
gacgcacaac tcgacgacta ccacgtcgac gccatcaccg gtgggaccga cgcggtcgtc  1380
accgtcgaag taaccatgtc tcacggcgac cgaagcgagc cagtcgccgc cgcgtacgcg  1440
gacatcaccc gtgcgagcgt gcaggcgatg gagcatgcgc tcgaccgact tctcgcgccg  1500
ggccataccg ctgcgtcacc agcatcggcc gacgactga                        1539
```

SEQ ID NO: 3              moltype = DNA   length = 1185
FEATURE                   Location/Qualifiers
source                    1..1185
                          mol_type = other DNA
                          organism = unidentified
SEQUENCE: 3

```
atgacgcgtg aagtggtagt ggtaagcggt gtccgtaccg cgatcgggac ctttggcggc   60
agcctgaagg atgtggcacc ggcggagctg ggcgcactgg tggtgcgcga ggcgctggcg  120
cgcgcgcagg tgtcgggcga cgatgtcggc cacgtggtat tcggcaacgt gatccagacc  180
gagccgcgcg acatgtatct gggccgcgtc gcggccgtca acggcggggt gacgatcaac  240
gcccccgcgc tgaccgtgaa ccgcctgtgc ggctcgggcc tgcaggccat tgtcagcgcc  300
gcgcagacca tcctgctggg cgataccgac gtcgccatcg gcggcggcgc ggaaagcatg  360
agccgcgcac cgtacctggc gccggcagcg cgctggggcg cacgcatggg cgacgccggc  420
ctggtcgaca tgatgctggg tgcgctgcac gatcccttcc atcgcatcca catgggcgtg  480
accgccgaga atgtcgccaa ggaatacgac atctcgcgcg cgcagcagga cgaggccgcg  540
ctggaatcgc accgccgcgc ttcggcagcg atcaaggccg gctacttcaa ggaccagatc  600
gtcccggtgg tgagcaaggg ccgcaagggc gacgtgacct tcgacaccga cgagcacgtg  660
cgccatgacg ccaccatcga cgacatgacc aagctcaggc cggtcttcgt caaggaaaac  720
ggcacggtca cggccggcaa tgcctcgggc ctgaacgacg ccgccgccgc ggtggtgatg  780
atggagcgcg ccgaagccga gcgcgcgggc ctgaagccgc tggcccgcct ggtgtcgtac  840
ggccatgccg gcgtggaccc gaaggccatg ggcatcggcc cggtgccggc gacgaagatc  900
gcgctggagc gcgccggcct gcaggtgtcg gacctggacg tgatcgaagc caacgaagcc  960
tttgccgcac aggcgtgcgc cgtgaccaag gcgctcggtc tggacccggc caaggttaac  1020
ccgaacggct cgggcatctc gctgggccac ccgatcggcg ccaccggtgc cctgatcacg  1080
gtgaaggcgc tgcatgagct gaaccgcgtg cagggccgct acgcgctggt gacgatgtgc  1140
atcggcggcg ggcagggcat tgccgccatc ttcgagcgta tctga                 1185
```

SEQ ID NO: 4              moltype = DNA   length = 285
FEATURE                   Location/Qualifiers
source                    1..285
                          mol_type = other DNA
                          organism = unidentified
SEQUENCE: 4

```
aagaaaccaa ttgtccatat tgcatcagac attgccgtca ctgcgtcttt tactggctct   60
tctcgctaac caaaccggta accccgctta ttaaaagcat tctgtaacaa agcgggacca  120
aagccatgac aaaaacgcgt aacaaaagtg tctataatca cggcagaaaa gtccacattg  180
attatttgca cggcgtcaca ctttgctatg ccatagcatt tttatccata agattagcgg  240
attctacctg acgcttttta tcgcaactct ctactgtttc tccat                 285
```

SEQ ID NO: 5              moltype = DNA   length = 20
FEATURE                   Location/Qualifiers
source                    1..20
                          mol_type = other DNA
                          organism = unidentified
SEQUENCE: 5

```
acaaccaaag gaggacaacc                                               20
```

SEQ ID NO: 6              moltype = DNA   length = 1158
FEATURE                   Location/Qualifiers
source                    1..1158
                          mol_type = other DNA
                          organism = unidentified
SEQUENCE: 6

```
atgtccgaag cgcaaccgct cgtcactccc aagcccaaga atccgtcgc cctgtcgggc    60
gtgaccgccg gcaataccgc gctgtgcacc gtcggccgca ctggcaacga cctgcactac  120
cgcggctacg acatcctcga catcgccgag acctgcgagt cgaggaaat cgcccacctg   180
ctggtgcacg gcaagctgcc gaccaaatcc gaactggccg cctacaaggc caagctcaag  240
agcctgcgcg gcctgcccgc caatgtgaag gccgcgttgg aatgggtgcc cgccagcgcc  300
cacccgatgg acgtgatgcg caccggcgtg tcggtgctgg gcaccgtgct gccggagaag  360
gaagaccaca acaccccggg cgcgcgcgac attgccgacc ggctgatggc cagcctcggc  420
tcgatgctgc tgtactggta ccactacagc cacaacggcc gccgtatcga agtcgaaacc  480
gacgatgact ccatcggcgg ccacttcctg cacctgctgc acggcgagaa gccgtcggcg  540
ctgtgggagc gcgccatgaa cacctcgctc aacctgtacg ccgagcacga gttcaacgcc  600
tcgaccttca ccgcccgcgt gatcgccggc acgggctcgg acatgtattc gtcgatcagc  660
ggcgccatcg cgcgcactgcg cggccccaag cacgcggcg ccaatgaagt cgcgttcgag   720
```

-continued

```
atccagaagc gctacgacaa ccccgacgag gcccaggccg acatcacgcg ccgcgtcgag 780
aacaaggaag tcgtgatcgg cttcggccac ccggtgtaca ccaccggcga cccgcgcaac 840
caggtgatca aggaagtggc gaagaagctg tcgaaggatg ccggctcgat gaagatgttt 900
gacatcgccg agcgcctgga aacggtgatg tgggacatca agaagatgtt cccgaacctg 960
gactggttca gcgcggtgag ctaccacatg atgggcgtgc ccgaggcgat gttcacgccg 1020
ctgttcgtga tcgcgcgtac ttcgggctgg gccgcgcaca ttatcgagca gcgcatcgac 1080
aacaagatca tccgcccgag cgccaactac accggtccgg agaacctgaa gttcgtgccg 1140
ctgaaggatc gcaagtaa                                               1158

SEQ ID NO: 7             moltype = DNA  length = 1197
FEATURE                  Location/Qualifiers
source                   1..1197
                         mol_type = other DNA
                         organism = unidentified
SEQUENCE: 7
atgtccgcct cgaagttcgc cgcacccgac gctgcaccg acgccacggc cagcgagccg 60
gccgcgcccc gggtcaagaa atccgtcgcc ctgtcgggcg tgaccgccgg caataccgcg 120
ctgtgcaccg tcggccgcac cggcaacgac ctgcactacc gcggctacga catcctcgac 180
atcgccgaga cctgcgagtt cgaggaaatc gcccacctgc tggtacacgg caagctgccg 240
accaaatccg aactggccgc ctacaaggcc aagctcaaga gcctgcgcgg cctgcccgcc 300
aatgtgaagg ccgcgttgga atgggtgccc gccagcgccc acccgatgga cgtgatgcgc 360
accggcgtgt cggtgctggg caccgtgctg ccggagaagg aagaccacaa caccccgggc 420
gcgcgcgaca ttgccgaccg gctgatggcc agcctcggct cgatgctgct gtactggtac 480
cactacagcc acaacggccg ccgtatcgaa gtcgaaaccg acgatgactc catcggcggc 540
cacttcctgc acctgctgca cggcgagaag ccgtcggcgc tgtgggagcg cgccatgcac 600
acctcgctca acctgtacgc cgagcacgag ttcaacgcct cgaccttcac cgacctcgac 660
atcgccggca cgggctcgga catgtattcg tcgatcagcg gcgccatcgg cgcgctgcgc 720
ggccccaagc acggcggcgc caatgaagtc gcgttcgaga tccagaagcg ctacgacaac 780
cccgacgagg cccaggccga catcacgcgc cgcgtcggga caaggaagt cgtgatcggc 840
ttcggccacc cggtgtacac caccggcgac ccgcgcaacc aggtgatcaa ggaagtggcg 900
aagaagctgt ctaaggatgc cggctcgatg aagatgttcg acatcgccga gcgcctggaa 960
acggtgatgt gggacatcaa gaagatgttc ccgaacctgg actggttcag cgcggtgagc 1020
taccacatga tgggcgtgcc gacggcgatg ttcacgccgc tgttcgtgat cgcgcgtact 1080
tcgggctggg ccgcgcacat tatcgagcag cgcatcgaca acaagatcat ccgcccgagc 1140
gccaactaca ccggtccgga gaacctgaag ttcgtgccga tcggcaagcg caagtga 1197

SEQ ID NO: 8             moltype = DNA  length = 48
FEATURE                  Location/Qualifiers
source                   1..48
                         mol_type = other DNA
                         organism = unidentified
SEQUENCE: 8
ctaggtttat acataggcga gtactctgtt atggagtcag atcttagc                 48

SEQ ID NO: 9             moltype = DNA  length = 20
FEATURE                  Location/Qualifiers
source                   1..20
                         mol_type = other DNA
                         organism = unidentified
SEQUENCE: 9
tcggctcgat gctgctgtac                                                20
```